US009968100B2

(12) United States Patent
Yoo et al.

(10) Patent No.: US 9,968,100 B2
(45) Date of Patent: May 15, 2018

(54) NATURAL ANTIMICROBIALS AND ARTICLE COMPRISING THE SAME

(71) Applicant: COWAY CO., LTD., Chungcheongnam-do (KR)

(72) Inventors: Jun-Young Yoo, Seoul (KR); Chan-Jung Park, Seoul (KR); Kyung-Hwan Lee, Seoul (KR)

(73) Assignee: Coway Co., Ltd (KR)

( * ) Notice: Subject to any disclaimer, the term of this patent is extended or adjusted under 35 U.S.C. 154(b) by 387 days.

(21) Appl. No.: 14/350,706

(22) PCT Filed: Sep. 28, 2012

(86) PCT No.: PCT/KR2012/007900
§ 371 (c)(1),
(2) Date: Apr. 9, 2014

(87) PCT Pub. No.: WO2013/069890
PCT Pub. Date: May 16, 2013

(65) Prior Publication Data
US 2014/0302184 A1 Oct. 9, 2014

(30) Foreign Application Priority Data

Nov. 9, 2011 (KR) .................. 10-2011-0116670

(51) Int. Cl.
*A01N 65/06* (2009.01)
(52) U.S. Cl.
CPC ............ *A01N 65/06* (2013.01); *Y02A 50/348* (2018.01)
(58) Field of Classification Search
None
See application file for complete search history.

(56) References Cited

U.S. PATENT DOCUMENTS

| 5,629,016 A * | 5/1997 | Fielden ................ A61K 9/0095 424/464 |
| 2001/0055628 A1 | 12/2001 | Hsu et al. |
| 2005/0019434 A1 | 1/2005 | Duvert et al. |
| 2006/0182775 A1 | 8/2006 | Everett |
| 2008/0274072 A1 * | 11/2008 | Manolas ................ A61L 9/012 424/76.9 |
| 2009/0001191 A1 * | 1/2009 | Gutovic ................ A44C 1/00 239/36 |
| 2010/0061896 A1 * | 3/2010 | Sassoon ............ A01M 1/2033 422/124 |

FOREIGN PATENT DOCUMENTS

| CN | 1406194 | 3/2003 |
| JP | 2001-114619 | 4/2001 |
| JP | 2004-505025 | 2/2004 |
| KR | 1020040027240 | 4/2004 |
| KR | 1020110107513 | 10/2011 |
| WO | WO 88/00795 | 2/1988 |
| WO | WO 98/56395 | 12/1998 |
| WO | WO 01/41728 | 6/2001 |
| WO | WO 02/09524 | 2/2002 |

OTHER PUBLICATIONS

"Aromatherapy and Essential Oil Diffusers" website (https://web.archive.org/web/20101209003639/http://aromaweb.com/articles/diffu.asp—Internet archived version from Dec. 9, 2010).*
Chinese Office Action dated Jun. 24, 2015 issued in counterpart application No. 201280049830.2, 14 pages.
PCT/ISA/237 Written Opinion issued on PCT/KR2012/007900 (pp. 3), dated Mar. 20, 2013.
Korean Office Action dated Mar. 15, 2018 issued in counterpart application No. 10-2011-0116670, 7 pages.

* cited by examiner

*Primary Examiner* — Susan Hoffman
(74) *Attorney, Agent, or Firm* — The Farrell Law Firm, P.C.

(57) ABSTRACT

There is provided a natural antimicrobial including a mixture of tree essential oils, soybean oil, and a residual hydrocarbon extract extracted from a rutaceae plant, wherein the mixture is supported in a supporter, and an article including the antimicrobial are provided. The antimicrobial is comprised of only natural materials, so it is harmless to human beings and environmentally friendly. Also, in the antimicrobial, tree essential oils is supported together with soybean carrier oil in a supporter, and thus, volatility of tree essential oils is controlled by the soybean oil, whereby the tree essential oils is naturally emitted to have an effective antibiosis for a long period of time. Thus, extra power, driving device (e.g., a fan), or the like, is not required to emit the tree essential oils. In addition, the antimicrobial is actively emitted in the air, having efficacy of continuously annihilate bacteria, virus, or the like.

5 Claims, 2 Drawing Sheets

NATURAL ANTIMICROBIALS AND ARTICLE COMPRISING THE SAME

This application is a National Phase Entry of PCT International Application No. PCT/KR2012/007900 filed Sep. 28, 2012, and claims priority to Korean Patent Application No. 10-2011-0116670 filed with the Korean Intellectual Property Office on Nov. 9, 2011, the content of each of which is incorporated herein by reference.

TECHNICAL FIELD

The present invention relates to a natural antimicrobial using tree essential oils and an article including the same, and more particularly, to a natural antimicrobial continuously generating an antimicrobial effect by naturally emitting an antimicrobial element, and an article including the same.

BACKGROUND ART

For an agreeable environment and human health, harmful materials surrounding a living environment due to natural causes or due to various causes resulting from industrialization are required to be removed.

Antimicrobials using chemicals having an antimicrobial function have largely been used in a method of removing harmful materials. Recently, however, as interest in environmental issues and health-related concerns has grown, antimicrobials using natural materials which are environmentally friendly and harmless to humans are preferred.

Essential oils extracted from trees (hereinafter, referred to as 'tree essential oils') have been generally known as natural antimicrobial substances. In particular, terpene, a tree essential oil, includes more than 100 chemical components, e.g., hydrocarbons, alcohols, aldehydes, esters, ketone, oxides, phenols, and the like, and has antimicrobial, antiviral, analgesic, phlegm discharge reduction, skin hygiene, anticepsis, blood-pressure reduction, sterilization, anti-inflammation, sedation, and other effects. However, in tree essential oils, in the form of oil extracted from trees, chemical concentrations may not be uniform, so their effectiveness as antimicrobial substances may deteriorate. Thus, conventionally, in order to improve the volatility of tree essential oils, an artificial chemical material such as an alcohol may be combined therewith as a solvent. However, such a chemical material may be harmful to humans and/or the environment, according to a degree of exposure, so the adjustment of volatility of tree essential oils using a natural material is required. Thus, a natural antimicrobial that naturally emits an antimicrobial element on a continual basis over a long period of time by controlling the volatility of tree essential oils is required.

DISCLOSURE

Technical Problem

An aspect of the present invention provides an antimicrobial continuously generating an antimicrobial effect though natural emissions by adjusting the volatility of tree essential oils.

An aspect of the present invention also provides an antimicrobial that emits an antimicrobial element without the necessity of an additional device.

An aspect of the present invention also provides an antimicrobial comprised of only natural materials.

An aspect of the present invention also provides an article including the foregoing antimicrobial.

Technical Solution

According to a first aspect of the present invention, there is provided an antimicrobial including a mixture of 80 wt % to 85 wt % tree essential oils from at least one species of tree selected from the group consisting of pine, nut pine, and a retinispora, 8 wt % to 10 wt % of soybean oil, and a residual hydrocarbon extract extracted from a rutaceae plant, wherein the mixture is supported in a supporter.

According to a second aspect of the present invention, in the first aspect, 200 parts by weight to 300 parts by weight of the mixture may be supported in 100 parts by weight of the supporter of the antimicrobial.

According to a third aspect of the present invention, in the first aspect, the supporter of the antimicrobial may be a woody material, a natural extract material, a pulp material, a fiber material, a gel material, or a mineral material.

According to a fourth aspect of the present invention, in the third aspect, the supporter is a wood cork.

According to a fifth aspect of the present invention, there is provided an article including an antimicrobial according to one of the first to fourth aspects.

According to a sixth aspect of the present invention, in the fifth aspect, the article includes a cartridge charged with an antimicrobial.

According to a seventh aspect of the present invention, in the sixth aspect, a diameter of each hole of the cartridge of the article may be 1.5 mm to 1.8 mm, and a total area of the holes may be 10% to 15% of the total area of a lateral surface of the cartridge.

According to an eighth aspect of the present invention, in the fifth aspect, the article may be an air purifier, a sterilizer, a bidet, or a humidifier.

Advantageous Effects

An antimicrobial according to embodiments of the present invention is made of only a natural material, so it is harmless to humans and environment friendly. Also, in the antimicrobial, tree essential oils are supported together with soybean carrier oil and a natural blender in a supporter, and thus, volatility of the tree essential oils is adjusted by the soybean carrier oil, whereby the tree essential oils can be naturally emitted equally for a certain period of time, specifically, to exhibit antimicrobial activity. Also, extra power, an additional driving device (e.g., a fan), or the like, is not required to emit the tree essential oils. Thus, for example, when the antimicrobial is actually applied to an article such as an air purifier, or the like, the antimicrobial itself is actively naturally emitted to provide an antibacterial function, no matter whether or not the article is operated with power or without power.

BEST MODE

Figure 1:
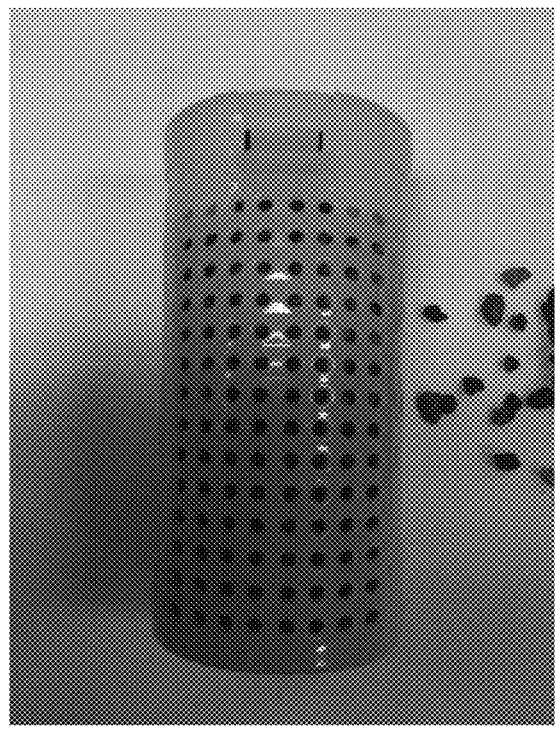
FIG. 1 is a photograph of a cartridge charged with an antimicrobial according to an embodiment of the present invention.

In an embodiment of the present invention, a mixture of tree essential oils, carrier oil, and a natural blender are supported in a supporter of an antimicrobial, whereby the volatility of tree essential oils is controlled to be continuously naturally emitted for a long period of time, providing an excellent antibacterial effect, and since the antimicrobial is comprised of only natural materials, it is environmentally friendly and harmless to humans.

The antimicrobial includes a supporter in which a mixture (hereinafter, referred to as an 'antimicrobial mixture') of tree essential oils of pine, nut pine, and retinispora, soybean oil, and a natural blender is supported.

Preferably, the supporter is made of a material of a homogeneous group as that of tree essential oils and soybean oil supported in the supporter, which has miscibility with the tree essential oils and soybean oil and excellent stability and is environmentally friendly. Also, preferably, the supporter is made of a porous material having high porosity (or air porosity) with high permeability and high adsorptive power exhibited when impregnated with the tree essential oils and soybean oil, having excellent durability such that the original form of the material is not depressed nor deformed when the tree essential oils are supported therein, and having excellent processibilty with respect to an array of processes such as molding, firing, sintering, and the like, as a component (or part). In addition, the material is required to have chemical resistance, non-toxicity, weather resistance, an attractive appearance, economic feasibility, an environment effect, and a structural design possibility in consideration of being attached to or detached from a cartridge.

The supporter is a natural supporting material that may be made of, for example, a woody material, a natural extract material, a pulp material, a fiber material, a gel material, or a mineral material, but the present invention is not limited thereto. The woody material may be, for example, a wood shavings fiber, a wood fiber mold block, a wood cork, a wood pellet, a wood powder, a cellulose pellet ball, a rice barn, active carbon, and the like, but the present invention is not limited thereto. The natural extract material may be, for example, xylitol, but the present invention is not limited thereto. The pulp material may be, for example, a pulp mold block, pulp felt, and bulky pulp, but the present invention is not limited thereto. The fiber material may be, for example, a cotton mold bloc, a cotton ball, a cotton flock, a cotton pad sheet, bomb yarn, lignous viscous rayon, ramie fiber, linen/flax, hemp fiber, and the like, but the present invention is not limited thereto. The gal material may be, for example, agar, konjakmannan, and the like, but the present invention is not limited thereto. The mineral material may be, for example, a pebble, a brook water stone, pumice, versicular vermiculate, an ocher ball, an ocher granule, a ceramic ball, zeolite, bentonite, illite, montmorillonite, rock salt, sodium nitrate (niter), silica gel, and the like, but the present invention is not limited thereto.

In the aspect of physical properties required for the supporter, preferably, a woody material, more preferably, wood cork, is used. Wood cork is especially desirous to be used as a supporter due to the following characteristics thereof. Namely, wood cork is a strong base material by itself, having excellent durability and having characteristics of not being decomposed. Also, wood cork has excellent chemical resistance with water, alcohol, acid, organic solvents, and since numerous cells are wrapped in a resin film, respectively, and aggregate densely, it has dense air gaps and excellent retaining force with respect to tree essential oils infiltrating into cork. In addition, wood cork is very flexible and has excellent physical elasticity and restoration to be returned to the original state thereof after pressure is applied thereto. Also, since wood cork has a honey-comb structure, it is less affected by impact or friction relative to a solid surface, and since it does not absorb dust, it is hypoallergenic and helps to prevent allergies. A shape, a size, and the like, of the supporter are not particularly limited and the supporter may be arbitrarily adjusted to have a desired shape and size.

An antimicrobial mixture, i.e., a mixture of tree essential oils, soybean oil, and a natural blender, is supported in the supporter. The tree essential oils, including terpene as an antimicrobial element, are oils extracted from trees, in particular, pinaceae, specifically, at least one selected from the group consisting of pine, nut pine, and a retinispora. Here, tree essential oils extracted from pine, nut pine, or a retinispora may be used alone or as a mixture of two or more types thereof. When the mixture is used, a mixture ratio of pine, nut pine, and retinispora oil is not particularly limited. The tree essential oils extracted from pine, nut pine, and a retinispora may have various effects useful for human bodies, such as a harmful material neutralization function, physiological activity, deodorization activity, sensitivity recognition activity, sterilization activity, aroma therapy activity, insect resistance activity, medical action, antiallergenic activity, anti-oxidant activity, antimicrobial activity, corrosion resistance activity and the like.

However, tree essential oils have high volatility, due to not having standardized or quantized volatility characteristics. Thus, the soybean oil is used together as a carrier oil for adjusting the volatility and viscosity of tree essential oils in the antimicrobial according to an embodiment of the present invention. The soybean oil has high solubility with respect to fat-soluble materials, and when it is combined with a natural material having high antiseptic effect and anti-oxidation such as tree essential oils, it exhibits excellent oxidation resistance, and since the soybean oil is a naturally avirulent material, it is preferably used as a carrier oil. Since the soybean oil having weak volatility is mixed with the tree essential oils, volatility of the tree essential oils may be decreased and a controlled amount of the mixture may be naturally emitted continually for a certain period of time, rather than being entirely evaporated within a short period of time.

Meanwhile, the tree essential oils and the carrier oil are stably mixed and, in addition, a natural blender is also mixed together in order to allow each element to exhibit effects for a longer period of time. As the natural blender, a hydrocarbon material, specifically, a hydrocarbon extract extracted from rutaceae, e.g., a sapindale plant species such as citrus fruit plants like orange and lime, is used.

As for the mixture of the tree essential oil, the soybean oil, and the natural blender, in consideration of volatility of the antimicrobial compound and emissions continuity of the antimicrobial element, specifically, an emissions continuity that maintains effective antimicrobial activity for at least 120 days and a minimum amount of emissions per day, 80 wt % to 85 wt % tree essential oils, 8 wt % to 10 wt % of soybean oil, and a residual natural blender are mixed such that a total mixed proportion of the antimicrobial compound is 100 wt %.

Also, in the aspect of the minimum amount of emissions of an antimicrobial element per day and securing durability, preferably, 200 parts by weight to 300 parts by weight of the antimicrobial mixture is supported over 100 parts by weight of the supporter.

The mixture of the tree essential oils and soybean oil may be supported in the supporter through any method generally known in the art. For example, the supporter may be immersed in the antimicrobial mixture to impregnate the supporter with the mixture of the tree essential oils and the soybean oil (or allow the mixture of the tree essential oils and the soybean oil to be absorbed into the supporter), but the present invention is not limited thereto. During the impregnation, the supporter and the mixture may be stirred together as necessary. Thereafter, the resultant material is dried obtain an antimicrobial according to an embodiment of the present invention. The impregnation is performed for about 24 hours to 30 hours at room temperature and at normal pressure to allow the antimicrobial mixture to be sufficiently mixed with the supporter. The mixture and the supporter are left for 24 hours to 72 hours at room temperature and at normal pressure to allow the mixture to evenly permeate into the supporter, which is then dried to obtain the antimicrobial according to an embodiment of the present invention. Performance, efficacy, and the like, of the antimicrobial may not be affected by preparation conditions such as temperature, pressure, humidity, and the like, but volatility (an amount of emissions, a rate of emissions, and the like) of the antimicrobial may differ according to the preparation conditions, so, preferably, the antimicrobial is prepared at room temperature and at normal pressure such that it cannot be damaged due to excessive volatility of the antimicrobial element when prepared.

The antimicrobial may be prepared in various forms according to an article to which the antimicrobial is applied and a purpose thereof. The antimicrobial may have a shape, for example, according to a shape of the supporter or may have a desired shape after prepared.

According to another embodiment of the present invention, an article including an antimicrobial according to an embodiment of the present invention is provided. The article may be any article intended to exhibit antimicrobial performance (or antibacterial performance). For example, the article may be an air purifier, a sterilizer, a bidet, a humidifier, and the like, but the present invention is not limited thereto.

For example, the antimicrobial may be charged in a cartridge, and the antimicrobial-charged cartridge may be installed in an article, thus being applied to the article, but the present invention is not limited thereto.

The cartridge has uniform holes on a lateral surface thereof. For example, the holes may have a size of, for example, 1.5 mm to 1.8 mm, in consideration of a shape, volatility, continual natural emission characteristics, and/or a minimum level of sterilization performance of the antimicrobial. Also, preferably, in the cartridge, a total area of the holes is about 10% to 15% of the total area of the lateral surface of the cartridge. In the case of using the antimicrobial, a size and a total area of the holes of the cartridge are adjusted to have the foregoing range such that about 0.03 or more of antimicrobial is emitted during a long period of time, e.g., until about 120 days have lapsed, or, for example, 0.5 g or more of the antimicrobial is emitted per day at an initial stage and 0.03 g or more of the antimicrobial is emitted when 120 days have passed, in general indoor daily environment conditions (room temperature and 30% to 60% of relative humidity). The minimum amount of emissions of the antimicrobial, i.e., 0.03 g, is a density for maintaining sufficient sterilizing power in an indoor space, for example, having an area of 33 m$^2$, which is calculated to be about tens to hundreds times of a minimum sterilization available density ($0.5 \times 10^{-9}$ ppm). FIG. 1 is a photograph of a cartridge charged with the antimicrobial.

The antimicrobial and the article including the same according to an embodiment of the present invention exhibit excellent antimicrobial (or antibacterial) and deodorization performance, and since volatility of the tree essential oils is optimally controlled by the soybean oil, the tree essential oils can be stably and continually naturally emitted. Thus, extra attached equipment such as power, fan, or the like, for the purpose of natural emissions is not required. Besides, since the antimicrobial is comprised of only natural materials, it is harmless to human beings and environmentally friendly.

[Mode for Invention]

Hereinafter, the present invention will be described in detail through an embodiment.

Embodiment 1

1. Preparation of Antimicrobial 12 g (80 wt %) of a mixture of tree essential oils extracted from pine and nut pine (a mixture ratio of pine oil:nut pine oil=4:1 wt %) and 1.5 g (10 wt %) of soybean oil were added to 1.5 g (10 wt %) of a hydrocarbon material extracted from orange plants as a natural blender, which were subsequently sufficiently mixed to obtain an antimicrobial mixture. Thereafter, the antimicrobial and 7.5 g of wood cork in the form of grains having a particle diameter ranging from Φ3 mm to Φ4.5 mm were stirred at room temperature, at normal pressure, with about 30% to 60% humidity, for about 24 hours to allow the mixture to be absorbed into the wood cork. Thereafter, the wood cork was dried at room temperature, at normal pressure, with about 30% to 60% humidity, for about 24 hours to obtain an antimicrobial.

2. Evaluation of Volatility (Natural Emission Characteristics)

The prepared antimicrobial was charged in cartridge having the shape as shown in FIG. 1 and having different total hole areas, as shown in Table 1 below. Thereafter, effective durability days (days in which an amount of emissions per day was 0.03 g or more) were evaluated by a difference between an amount (22.5 g) of the initially charged antimicrobial and a remaining antimicrobial with the lapse of time. Meanwhile, the amounts of emissions per day during the first 10 days were averaged to evaluate it as an average amount of emissions during the first 10 days. A capacity of the cartridge was 0.81 cm$^3$, a diameter of each hole of the cartridge ranged from 1.5 mm to 1.8 mm, and a total area of the holes was a relative value over the total area of the lateral surface of the cartridge.

TABLE 1

| Test No. | Total hole area | Average amount of emissions during first 10 days | Effective durability days |
| --- | --- | --- | --- |
| (1) | 100% | 0.8675 g | 20 days |
| (2) | 43.5% | 0.5792 g | 46 days |
| (3) | 15% | 0.3892 g | 134 days |

As shown in Table 1 above, when the hole areas were 100% and 43.5%, volatility of the antimicrobial was not controlled and the antimicrobial element was entirely emitted within a few days, resulting in a failure of obtaining a continual antimicrobial effect. However, when the area of the holes of the cartridge was 15%, it can be seen that, days during which an amount of emissions per day was 0.03 g were 134 days, so volatility of the antimicrobial was appropriately controlled and the effective antibiosis was maintained for a long period of time.

3. Evaluation of Antibiosis

Blood agar plates of strain of *E. Coli, Klebsiella pneumonia,* and *Hemophilus influenza* and the cartridge charged with the antimicrobial of test No. (3) of the volatility evaluation were positioned in a purified chamber having a size of 9.6 m$^3$, and removal of fungi with the lapse of time was observed.

Figure 2:
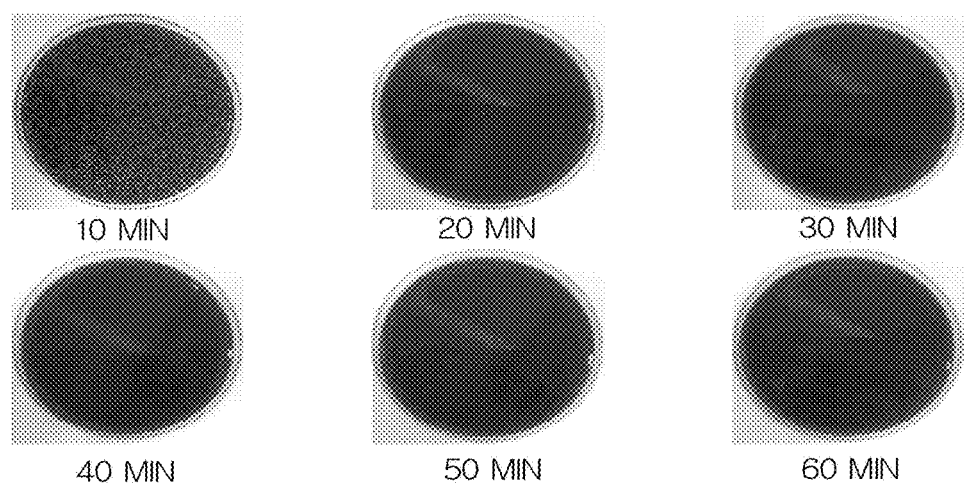
FIG. 2 is a photograph showing an *E. Coli* sterilization effect.
Figure 3:
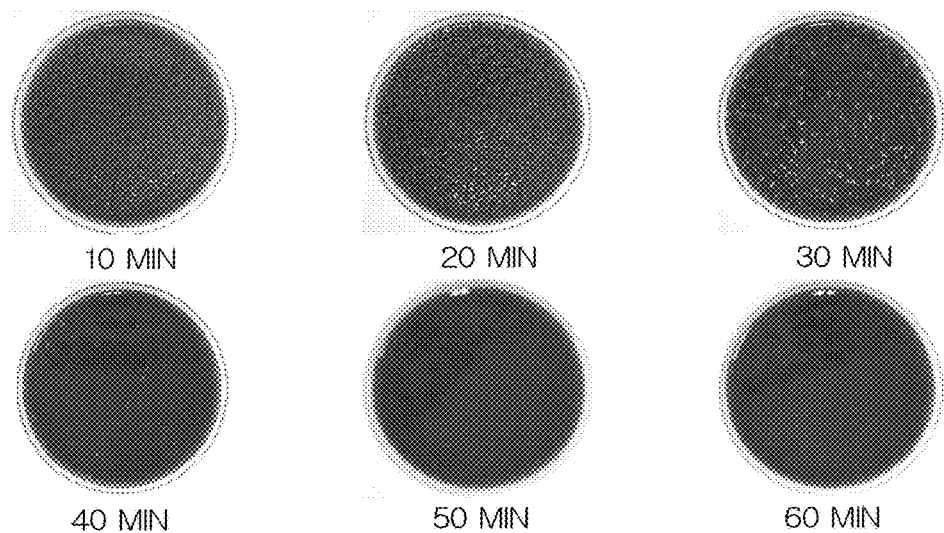
FIG. 3 is a photograph of a *Klebsiella pneumonia* sterilization effect.
Figure 4:
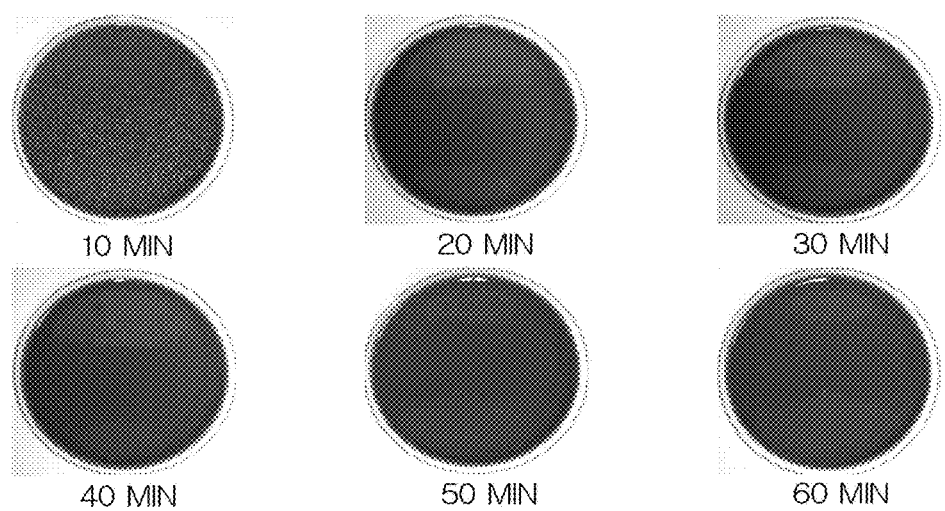
FIG. 4 is a photograph of a *Hemophilus influenza* sterilization effect over.

FIGS. 2 through 4 show photographs of the blood agar plates over time. FIG. 2 shows a sterilization effect of *E. Coli,* and colon bacillus (or *E. Coli*) was not observed after the lapse of about 20 minutes. FIG. 3 shows a sterilization effect of *Klebsiella pneumonia,* and when about 40 minutes were lapsed, strain was considerably reduced. FIG. 4 shows a sterilization effect of *Hemophilus influenza,* and when about 20 minutes were lapsed, no strain was observed. In this manner, the antimicrobial according to an embodiment of the present invention had excellent antimicrobial effect.

Embodiment 2

4.8 g (80%) of tree essential oils extracted from retinispora and 0.6 g (10%) of soybean oil were added to 0.6 g (10%) of hydrocarbon material extracted from lime as a natural blender, and then, sufficiently mixed to obtain an antimicrobial mixture. Thereafter, the antimicrobial mixture and 3 g of wood shavings fiber in the form of a heterogeneous scob having a size of 3 mm to 10 mm were stirred at room temperature, at normal pressure, with 30% to 60% humidity, for about 24 hours to allow the mixture to be absorbed into the wood shavings fiber. Thereafter, the wood shavings fiber was dried at room temperature, at normal pressure, with 30% to 60% humidity, for about 24 hours to obtain an antimicrobial.

Meanwhile, antibiosis was evaluated in the same manner as that of Embodiment 1, and also, in the case of Embodiment 2, antimicrobial effect with respect to *E. Coli, Klebsiella pneumonia,* and *Hemophilus influenza* was confirmed, like Embodiment 1.

When the antimicrobial was charged and used in the cartridge that holes each having a diameter ranging from 1.5 mm to 1.8 mm and a total area of the holes is about 10% to 15% over a total area of a lateral surface of the cartridge, natural emission characteristics exhibiting antibiosis were effective (or valid) for a long period of time, specifically, for about 4 months.

The invention claimed is:

1. An antimicrobial including an antimicrobial mixture impregnated in a porous support element,
    the antimicrobial mixture consisting of 80 wt % to 85 wt % tree essential oil from a pine, 8 wt % to 10 wt % of soybean oil, and the remainder of the antimicrobial mixture, to 100 wt %, being a hydrocarbon extract extracted from a rutaceae plant,
    wherein the rutaceae plant is at least one selected from the group consisting of an orange and a lime,
    wherein 200 parts by weight to 300 parts by weight of the mixture is impregnated in 100parts by weight of the porous support element of the antimicrobial, and
    wherein the support element is formed of wood cork.

2. An article including the antimicrobial of claim 1.

3. The article of claim 2, wherein the article includes a cartridge charged with the antimicrobial.

4. The article of claim 3, wherein the cartridge has holes, and
    wherein a diameter of each hole of the cartridge ranges from 1.5 mm to 1.8 mm, and a total area of the holes is 10% to 15% of the total area of a lateral surface of the cartridge.

5. The article of claim 2, wherein the article is one of an air purifier, a sterilizer, a bidet, and a humidifier.

* * * * *